(12) United States Patent
Tsutsui

(10) Patent No.: US 7,806,117 B2
(45) Date of Patent: Oct. 5, 2010

(54) PERORAL POWDER DELIVERY DEVICE

(75) Inventor: Tatsuo Tsutsui, Yokohama (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 1072 days.

(21) Appl. No.: 11/422,770

(22) Filed: Jun. 7, 2006

(65) Prior Publication Data

US 2007/0283955 A1 Dec. 13, 2007

(51) Int. Cl.
*A61M 15/00* (2006.01)
*A61M 16/00* (2006.01)

(52) U.S. Cl. .......................... 128/203.21; 128/203.15; 128/203.12; 128/200.24

(58) Field of Classification Search ............ 128/203.12, 128/203.15, 203.21, 203.22, 203.23, 200.17, 128/200.18, 200.22; 251/61.4, 63.4; 137/540; 604/54, 57, 58, 94, 516, 244

See application file for complete search history.

(56) References Cited

U.S. PATENT DOCUMENTS

| | | | | |
|---|---|---|---|---|
| 3,906,950 A | * | 9/1975 | Cocozza ................ | 128/203.15 |
| 3,949,751 A | * | 4/1976 | Birch et al. ............ | 128/203.15 |
| 4,446,862 A | * | 5/1984 | Baum et al. ........... | 128/203.15 |
| 4,889,114 A | * | 12/1989 | Kladders ............... | 128/203.15 |
| 5,651,359 A | * | 7/1997 | Bougamont et al. .... | 128/203.15 |
| 5,685,294 A | * | 11/1997 | Gupte et al. ........... | 128/203.15 |
| 5,715,811 A | | 2/1998 | Ohki et al. | |
| 5,752,505 A | * | 5/1998 | Ohki et al. ............. | 128/203.15 |
| 5,881,721 A | * | 3/1999 | Bunce et al. ........... | 128/203.21 |
| 5,989,217 A | * | 11/1999 | Ohki et al. ............. | 604/94.01 |
| 6,105,929 A | * | 8/2000 | Davenport et al. ........ | 251/63.6 |
| 6,408,846 B1 | * | 6/2002 | Ohki et al. ............. | 128/203.15 |
| 6,629,529 B2 | * | 10/2003 | Arnott .................. | 128/204.23 |
| 6,810,872 B1 | * | 11/2004 | Ohki et al. ............. | 128/203.15 |
| 7,278,982 B2 | * | 10/2007 | Tsutsui .................. | 604/58 |
| 7,353,823 B2 | * | 4/2008 | Tsutsui .................. | 128/203.21 |
| 2005/0177095 A1 | | 8/2005 | Tsutsui | |
| 2006/0000473 A1 | * | 1/2006 | Myrman ................ | 128/203.15 |

FOREIGN PATENT DOCUMENTS

| | | |
|---|---|---|
| JP | 7-313599 | 12/1995 |
| JP | 3372105 | 11/2002 |

OTHER PUBLICATIONS

English Language Abstract of JP 7-313599.

* cited by examiner

*Primary Examiner*—Justine R Yu
*Assistant Examiner*—Annette F Dixon
(74) *Attorney, Agent, or Firm*—Greenblum & Bernstein P.L.C.

(57) ABSTRACT

A peroral powder delivery device having a capsule holder for loading the capsule into a body is attached so as to be capable of advancing into and retracting from the inside of the body, the body has a cutter blade to make holes on both ends of the capsule as it advances into the body being held by the capsule holder, first and second air passageways having connection ports in communication with the holes in the capsule loaded in the body, the first air passageway has an inhaling port for inhaling the peroral powder in the capsule and the second air passageway has a suction valve that opens by the inhaling force from an inhaling port introduce air into the capsule.

5 Claims, 7 Drawing Sheets

PERORAL POWDER DELIVERY DEVICE

BACKGROUND OF THE INVENTION

1. Field of the Invention

The present invention concerns a peroral powder delivery device to deliver a peroral powder such as a powdery medicine or a powdery supplement, through an oral cavity.

2. Description of the Related Art

As one of methods of dosing a medicine to lungs of asthma patients, etc., a method to inhale a unit dose of powdery medicine in a capsule by making holes in the capsule has been known and, as a delivery device used for the dosing method, an inhaling type dosing device, for example, as shown in FIG. 8 and FIG. 9 has been proposed (refer to JP No. 3372105).

The delivery device includes a body 80 for loading a capsule C that contains a powdery medicine, a capsule holder 81 that holds the capsule C to be loaded in the body 80, and a hole making member 82 having a pair of pins 83, 83 to pierce the body of the capsule C which is loaded being held by the capsule holder 81 in the body so. Upon dosing the powdery medicine contained in the capsule C into lungs through an oral cavity, a cylindrical capsule holder 81 is at first fitted to a cylindrical holder receiving section 84 formed to the body 80, the capsule C is inserted into a capsule receiving bore 85 formed along the central axis of the capsule holder 81. Then, a pair of pin insertion holes 86, 86 formed in the peripheral wall of the holder receiving section 84 and a pair of pin insertion holds 87, 87 formed so as to pierce the peripheral wall of the capsule holder 81 are positioned so as to be in communication with each other. Then, pins 83, 83 of the hole making member 82 are inserted from the pin insertion holes 86, 86 of the holder receiving section 84 into the pin insertion holes 87, 87 of the capsule holder 81, thereby making four holes in total in the body of the capsule C held in the capsule receiving bore 85 of the capsule holder 81. Then, the pins 83, 83 of the hole making member 82 are withdrawn from the pin insertion holes 87, 87 to attain a state where the pins are remained in the pin insertion holes 86, 86. In this state, an inhaling port 89 of an inhaling mouth piece 88 formed integrally with the holder receiving section 84 of the body 80 is put in a patient's mouth for inhalation of the powder.

Thus, air is sucked into the inhaling mouth piece 88 through a pair of air passageways 90, 90 which are formed in parallel with each other on both sides of the capsule receiving bore 85 in perpendicular to the pin insertion holes 87, 87 of the capsule holder 81, and a portion of air passing the air passageways 90, 90 flows through the inside of the pierced body of the capsule C, by which the powdery medicine is discharged from the inside of the capsule C, inhaled from the inhaling port 89 of the inhaling mouth piece 88, and dosed into lungs.

Then, in a case of ejecting the spent capsule C from the capsule receiving bore 85 of the capsule holder 81, the capsule holder 81 is at first drawn out of the holder receiving section 84 of the body 80. Then, a needle is inserted from a small hole 91 opened at the bottom of the capsule receiving bore 85 of the capsule holder 81 into the capsule receiving bore 85 thereby pushing out the capsule C held in the capsule receiving bore 85.

However, since the delivery device described above is extremely complicated in the structure and needs a number of individual parts, it involves a drawback that the manufacturing cost is extremely expensive. Further, the operation procedure of the device is also extremely complicated and it requires troublesome operations, upon making holes in the capsule C, of positioning the pin insertion holes 8G, 86 formed in the holder receiving section 84 of the body 80 and the pin insertion holes 87, 87 formed in the capsule holder 81 to be fitted in the holder receiving section 84 so as to be in communication with each other and inserting the pins 83, 83 of the hole making member 82 into the pin insertion holes 86, 86 and 87, 87.

Further, after making the holes in the capsule C, it is necessary for extracting the pins 83, 83 of the hole making member 82 from the pin insertion holes 87, 87 thereby making the holes of the capsule C and the air passageways 90, 90 closed so far by the pins 83, 83, while leaving the top ends of the pins 83, 83 in the pin insertion holes 86, 86 in order not to open the pin insertion holes 86, 86 in communication with the air passageway 90 by way of the pin insertion holes 87, 87. With no such operations, the powdery medicine in the capsule C can not be inhaled. In a case where the pins 83, 83 are not completely extracted out of the pin insertion holes 87, 87 or in a case where the pins 83, 83 are drawn out erroneously also from the pin insertion holes 86, 86, it is difficult to inhale the powdery medicine in the capsule C.

Further, also in a case of ejecting the spent capsule C through the capsule receiving bore 85 of the capsule holder 81, it requires a troublesome operation of inserting the needle from the small hole 91 opened at the bottom of the capsule receiving bore 85 and pushing out the capsule C.

Further, since the dosing device described above has such a structure that respective parts of the body 80, the capsule holder 81, and the hole making member 82 are separated from each other, it may be a worry that the device can no more be used when any one of the parts is lost. Further, since the capsule C is made holes by piercing the pins 83, 83 of the hole making member 82, burrs of the capsule C formed upon piercing the pin 83 protrude to the periphery of the holes to hinder the flow of air flowing inside the capsule C. Further, since air flowing through the capsule C upon inhalation by putting an inhaling port 89 of an inhaling mouth piece 88 in the mouth flows inward and outward by way of the pin insertion holes 87, 87 which are perpendicular to the air passageways 90, 90, neither large flow volume nor high flow velocity can be produced. Accordingly, this may cause a disadvantage that the powder in the capsule C is not discharged thoroughly but remains partially in the capsule C and the necessary amount of the medicine is not dosed into the lungs, or a disadvantage that the particle of the powdery medicine can not be dosed in a finely separated and dispersed state.

Further, it may be a worry that the powder in the capsule C is spilt by its own weight from the holes made in the capsule C, scatters into the pin insertion holes 87, 87 and leaks to the outside passing through the air passageways 90, 90 in communication with the pin insertion holes 87, 87. It also involves a drawback that the powder in the capsule C flows to the outside in a case of erroneously blowing breath from the inhaling port 89 of the inhaling mouth piece 88.

By the way, various powdery supplements prepared by powdering dietary supplements intended for easy intake of ingredients such as amino acids, proteins, anti-oxidants, various kinds of vitamins and minerals have been marketed recently. Such powdery supplements include those incorporated in bottles or in capsules. Since it is desirable to continuously intake supplements at a predetermined amount on every times for attaining good physical balance or improving the physical conditions, the intake amount is controlled by using a spatula or the like for the bottle-incorporated powdery supplements and by the number of the capsules to be taken in a case of encapsulated powdery supplements.

However, the bottle-incorporated powdery supplement is inconvenient to carry about and it is troublesome to take while measuring the intake amount on every times by the spatula. Further, while the encapsulated powdery supplement is convenient to carry about, since it is intaken together with the capsule, this is not suitable to those who feel difficulty in swallowing capsules.

SUMMARY OF THE INVENTION

The present invention intends to provide a peroral powder delivery device having the capability to completely aspirate a peroral powder in the capsule through an oral cavity with simple operation to make holes in a capsule that contains a peroral powder such as a powdery medicine or a powdery supplement, the reduced manufacturing cost based on a simple structure, and a user-friendly operation. This is one of principal technical subjects of the invention.

The present invention provides a peroral powder delivery device to dose a unit dose of a peroral powder through an oral cavity, in which a capsule holder for holding a capsule that contains a peroral powder and loading the capsule in the body is attached in the body such that it can advance to and retract from the inside of the body in the direction perpendicular to the longitudinal direction of the capsule held by the capsule holder, the body has cutter blades for cutting both ends of the capsule when it advances being held by the capsule holder to the inside of the body, thereby making holes on both ends thereof, and a first air passageway having a connection port in communication with a hole made at one end of the capsule and a second air passageway having a connection port in communication with a hole made at the other end of the capsule when the capsule is loaded inside the body, the first air passageway has an inhaling port for inhaling the peroral powder in the capsule, and the second air passageway has a suction valve which is opened by a suction force from the inhaling port to introduce air into the capsule.

In the peroral powder delivery device according to the invention, both ends of the capsule are cut by the cutter blade and made holes on both ends thereof and, at the same time, the holes made on both ends are in communication with the connection port of the first air passageway and the connection port of the second air passageway formed in the body respectively by a simple operation of merely advancing the capsule holder into the body and loading the capsule that contains the peroral powder being held by the capsule holder in the inside of the body In this state, when an inhaling port formed to the first air passageway is sucked via a mouth, the suction valve disposed to the second air passageway is opened by the suction force to introduce air into the capsule and, at the same time, the peroral powder in the capsule is inhaled from the inhaling port to the inside of the oral cavity. After dosing the peroral powder in the capsule through the oral cavity, the spent capsule held by the capsule holder can be ejected simply by merely retracting the capsule holder from the inside of the body.

Accordingly, since the delivery device of the invention can conduct the operation of loading or discharging the capsule or the operating of making holes in the capsule by one-touch and the method of using the device is also extremely simple, there is no worry of erroneous operation. Further, since the capsule holder for holding the capsule is attached so as to be capable of advancing to and retracting from the inside of the body and the cutter blade to make holes in the capsule is also formed integrally to the body, there is no worry that the delivery device becomes unusable when losing any one of the capsule holder, the body, and the cutter.

Further, since the delivery device according to the invention is remarkably simplified compared with the existent delivery device described above in the structure, the manufacturing cost can be reduced remarkably. Further, since the first air passageway having the inhaling port, the inside of the capsule made holes at both ends, and the second air passageway having the suction valve are connected in series, the peroral powder in the capsule can be sucked to the outside efficiently by the inhaling force from the inhaling port and, scattering of the peroral powder in the capsule to the outside of the body can be prevented by the suction valve, the peroral powder can be dosed instantaneously with no loss.

PREFERRED EMBODIMENTS OF THE INVENTION

In a preferred embodiment of a peroral powder delivery device according to the present invention, a capsule holder for holding a capsule that contains a peroral powder to be dosed through an oral cavity slidably in the longitudinal direction and loading the capsule to the inside of the body is attached to the body so as to be capable of advancing to and retracting from the inside of the body along a direction perpendicular to the longitudinal direction of the capsule, the body has a cutter blade for cutting the both ends of the capsule that advances into the body being held by the capsule holder to make holes on both ends thereof, and a positioning guide for sliding the capsule that advances into the body being held by the capsule holder in the longitudinal direction and guiding both ends of the capsule to be cut by the cutter blade such that both ends of the capsule situate at predetermined positions, and a first air passageway having a connection port in communication with the hole made at one end of the capsule and a second air passageway having a connection port in communication with the hole made at the other end of the capsule when the capsule is loaded in the body, the first air passageway has an inhaling port for inhaling the peroral powder in the capsule, and the second air passageway has a suction valve that opens by the inhaling force from the inhaling port and introduces air into the capsule.

Further, the distance between the connection port of the first air passageway and the connection port of the second air passageway is set shorter than the length of the capsule after the both ends have been cut by the cutter blade such that the both ends of the capsule loaded therebetween are pressed by the peripheral edges of both of the connection ports, and the diameter of the holes made on both ends of the capsule by the cutter blade is set substantially identical with or larger than the opening diameter for each of the connection ports in communication with the hole. Further, the suction valve has a disciform poppet that protrudes from the suction port of the second air passageway and advances from the hole in communication with the suction port into the cavity upon opening of the valve.

Further, the cutter blade comprises a pair of blades secured in parallel with each other in the direction opposing to the advancing direction of the capsule that advances into the body being held by the capsule holder. The positioning guide comprises a pair of protrusions and a pocket is formed between the blade member and the protrusion disposed on near side thereof for discharging the cut ends of the capsule cut by the blade. Further, the first air passageway has a mixer chamber formed to the air passageway for generating a turbulent flow to air inhaled from the inhaling port thereby finely separating and dispersing the particle of the peroral powder inhaled together with air from the inside of the capsule.

DESCRIPTION OF THE ACCOMPANYING DRAWINGS

DESCRIPTION OF PREFERRED EXAMPLES OF THE INVENTION

Example 1

Figure 1:
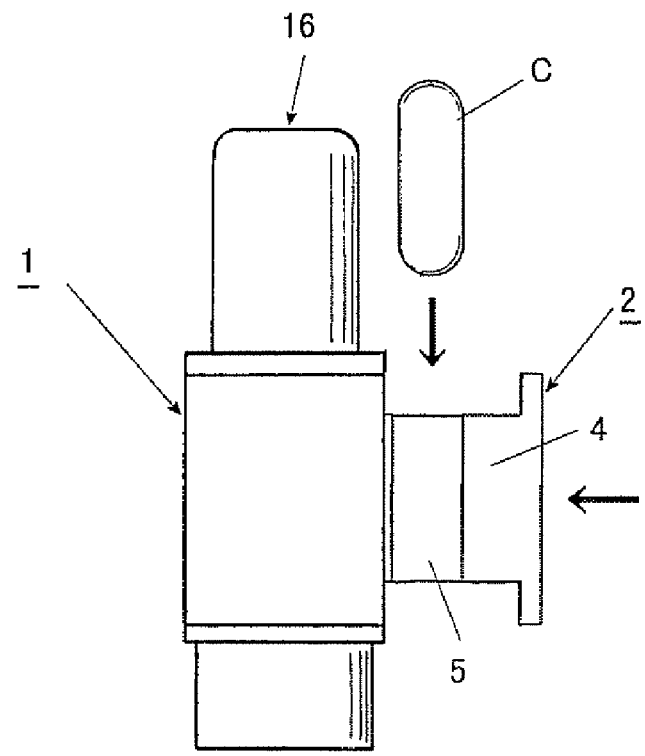
FIG. 1 is an external view showing an example of a peroral powder delivery device according to the present invention.

Example 1 of the present invention is to be described in conjunction with the appended drawings from FIG. 1 through FIG. 6.

In a peroral powder delivery device according to this example, a capsule holder 2 for loading a capsule C containing a peroral powder P such as a powdery medicine or a powdery supplement to be dosed through an oral cavity is loaded to the body 1 in the direction perpendicular to the longitudinal direction of the capsule C held by the capsule holder 2 so as to be capable of advancing to and retracting from the inside of the body 1. Further, the capsule holder 2 includes a drawer type plate 4 to be put in and out of the space 3 inside the body 1 for loading the capsule C. A recessed groove 5 is formed to the surface of the plate 4 for slidably holding the capsule C in the longitudinal direction with both ends of the capsule C protruding from the end edges of the plate 4. A protrusion 7 is formed to the back surface of the plate 4 for engagement with a stopper protrusion 6 formed at the inlet of the space 3 in the body 1 such that the plate 4 does not fall off the body 1. A guide groove 8 is formed for slidably guiding and supporting the plate 4 in engagement with the stopper protrusion 6 in the direction of putting into and out of the space 3 in the body 1.

The body 1 has cutter blades 10a, 10b for cutting both ends of the capsule C that advances into the body 1 while being held by the capsule holder 2 thereby making holes 9a, 9b on both ends thereof. The body 1 also has positioning guides 11a, 11b on the near side of the cutter blades 10a, 10b sliding the capsule that advances into the body 1 being held in the recessed groove 5 of the capsule holder 2 in the longitudinal direction and guiding both ends of the capsule C to be cut by the cutter blades 10a, 10b such that both ends of the capsule C situate at predetermined positions. The cutter blades 10a and 10b comprises a pair of blades secured in parallel with each other with the blade tips being directed in the direction opposing to the advancing direction of the capsule C that advances into the body 1 while being held by the capsule holder 2. The positioning guides 11a and 11b are formed of a pair of protrusions. Further, pockets 12a, 12b are formed each between the blade forming the cutter 10a or 10b and the protrusion forming the positioning guide 11a or 11b disposed on the near side thereof for discharging cut ends of the capsule C cut by the blade.

Further, the body 1 has a first air passageway 14 having a connection port 13a in communication with the hole 9a made on one end of the capsule C and a second air passageway 15 having a connection port 13b in communication with the hole 9b made on the other end of the capsule C. The first air passageway 14 has an inhaling port 16 for inhaling the peroral powder P in the capsule C, and the second air passageway 15 has a suction valve 17 that opens by the suction force from the inhaling port 16 to introduce air into the capsule C. The suction valve 17 is adopted such that a valve body 18 is resiliently biased in the direction of closing the valve by a spring 20 and opened against the resiliency of the spring 20 by the suction force upon inhalation at the inhaling port 16 via a mouth. Further, the valve has a disciform poppet 19 that protrudes upon opening from the connection port 13b of the second air passageway 15 and can advance from the hole 9b of the capsule C in communication with the suction port 13b into the capsule C.

The distance between the positioning guides 11a and 11b is set to a distance corresponding to the shortest length of the capsule that varies during manufacture of capsules Further, the cutter blades 10a, 10b are arranged at such positions that they can cut off the tops of the spherical surface forming both ends of the capsule C situated to the predetermined position by the positioning guides 11a, 11b each for a predetermined area thereby capable of making the holes 9a and 9b each having a diameter substantially equal with or slightly larger than the opening diameter of the connection ports 13a and 13b to both ends of the capsule C. That is, the diameters for the holes 9a, 9b made on both ends of the capsule C by the cutters 10a, 10b are set each to a size substantially identical with or larger than the opening diameter of the connection holes 13a, 13b in communication with the holes 9a, 9b.

Further, the distance M between the connection port 13a and the connection port 13b is set to a size smaller than the distance L between the blade tips of the cutters 10a, 10b for cutting off both ends of the capsule C. That is, the distance M between the connection ports 13a and 13b is set shorter than the length of the capsule C after the both ends thereof have been cut by the cutters 10a, 10b, such thon both ends of the capsule C loaded between the connection ports 13a and 13b are pressed by the peripheral edges 21a and 21b of both of the connection ports 13a and 13b.

Figure 2:
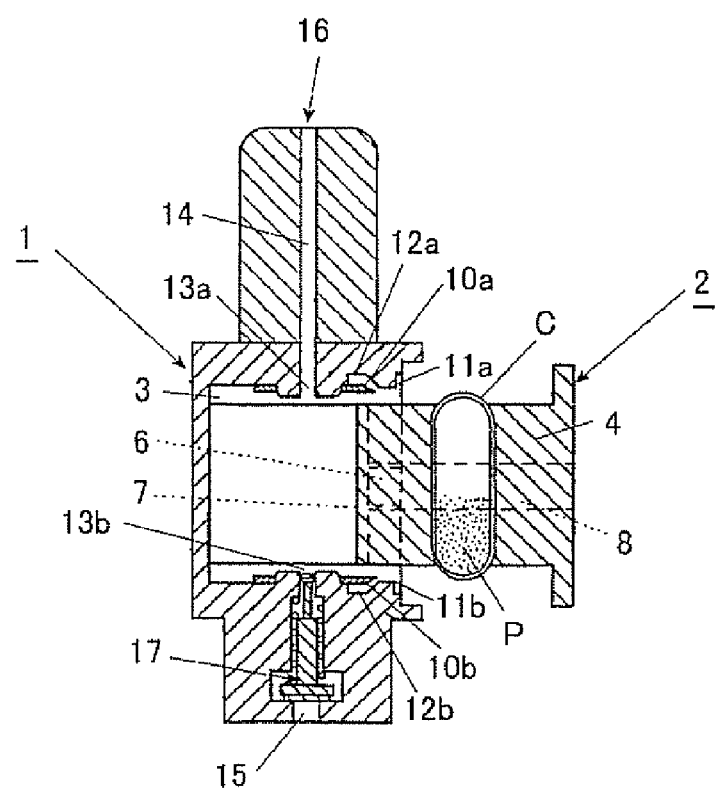
FIG. 2 is a cross sectional view of FIG. 1.
Figure 3:
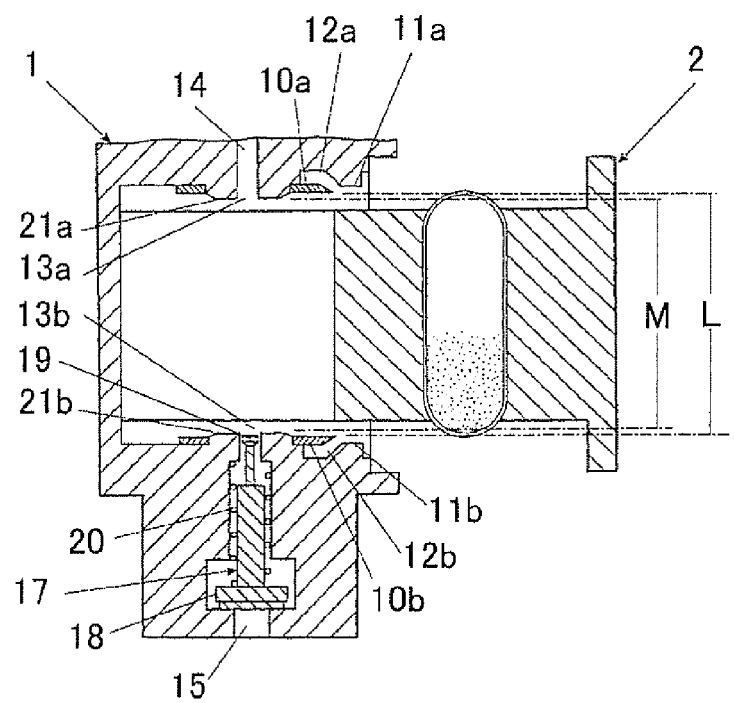
FIG. 3 is a fragmentary enlarged view of FIG. 2.

The constitution of the peroral powder delivery device shown in FIG. 1 to FIG. 6 is as has been described above, and the method of use and the operation of the delivery device are to be described below. As shown in FIG. 1 to FIG. 3, the peroral powder b in the capsule C can be inhaled from the inhaling port 16 of the body 1 by extremely simple operations of merely retracting the capsule holder 2 from the inside of the body 1 so as to put the drawing type plate 4 out of the space 3 inside the body 1, then holding the capsule C containing a predetermined amount of the peroral powder P in the recessed groove 5 of the plate 4, and advancing the capsule holder 2 into the body 1 so as to push the plate 4 into the space 3 of the body 1.

Figure 4:
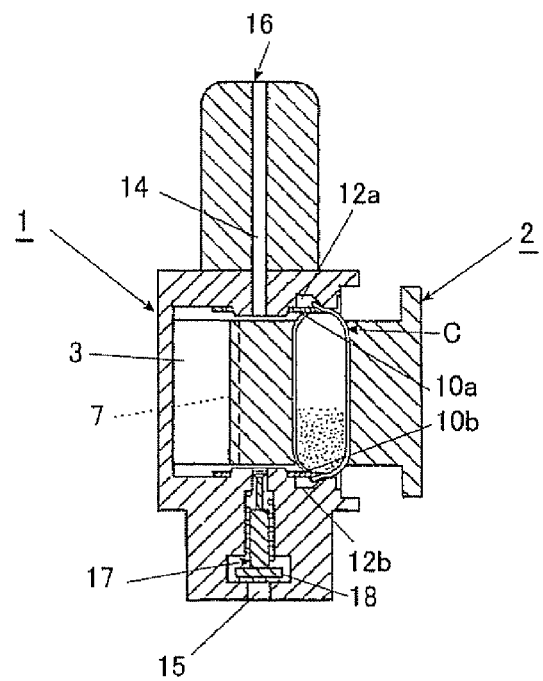
FIG. 4 is a cross sectional view in a state where holes are made on both ends of a capsule by a cutter blade.
Figure 5:
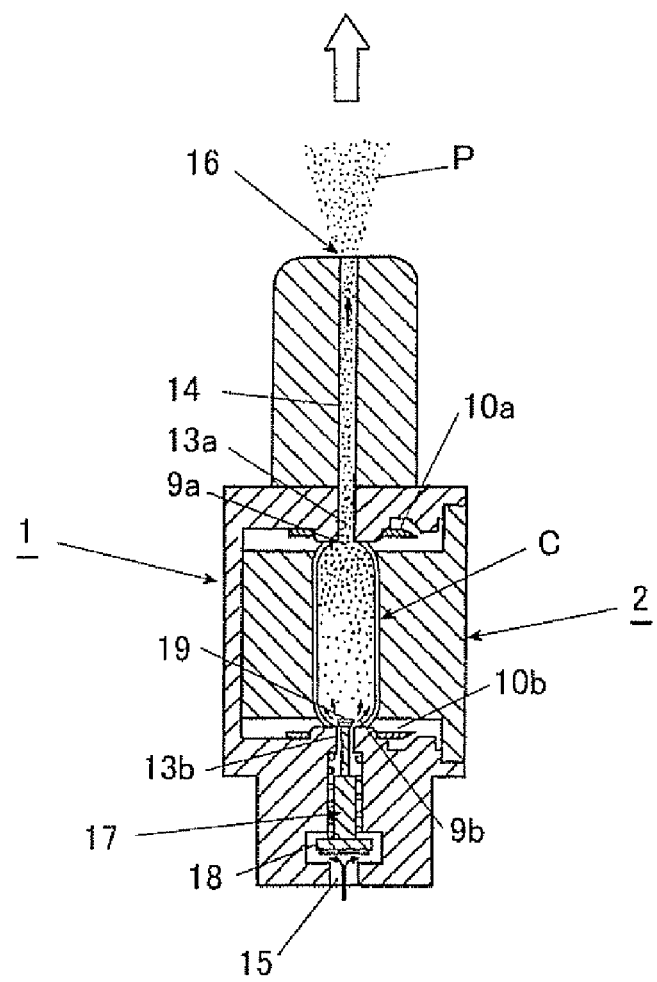
FIG. 5 is a cross sectional view in a state where a capsule is loaded in a body and a power is inhaled from an inhaling port.
Figure 6:
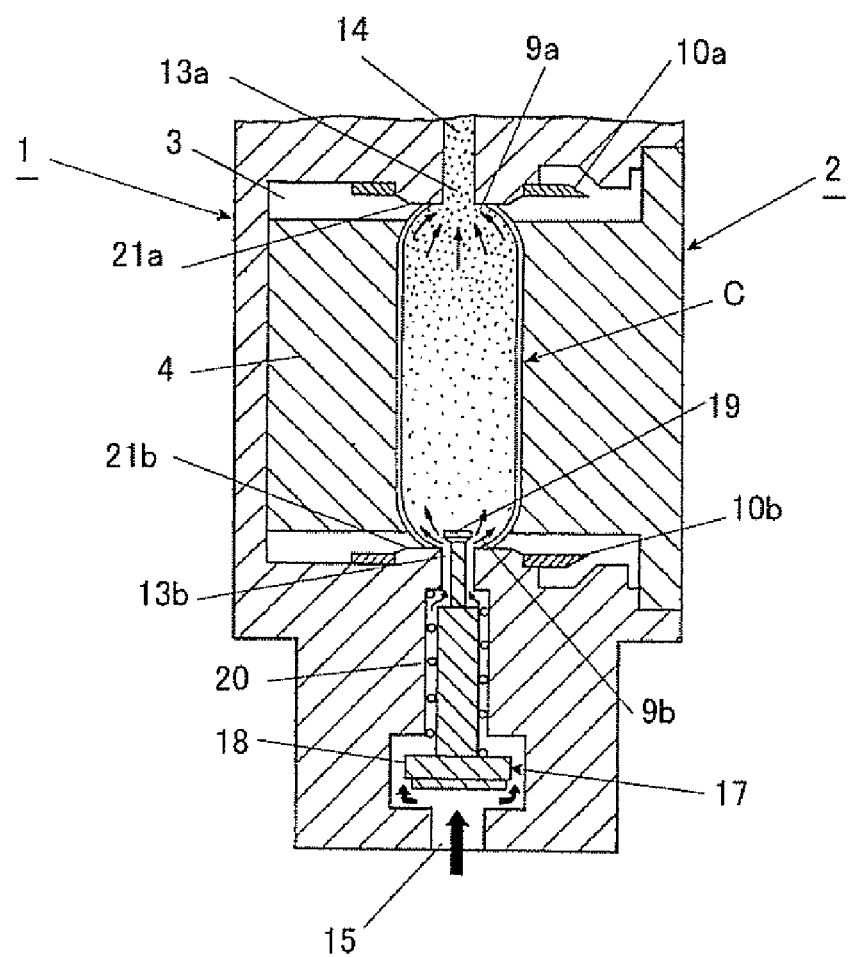
FIG. 6 is a fragmentary enlarged view of FIG. 5.

That is, when the capsule holder 2 holding the capsule C in the recessed groove 5 of the plate 4 is advanced into the body 1, both ends of the capsule C are caused to slid till predetermined positions being guided by the positioning guide 11a, 11b, the both ends are cut by the cutters 10a, 10b as shown in FIG. 4, and the holes 9a, 9b each having a diameter substantially equal with or slightly larger than the opening diameter of the connection ports 13a, 13b are made at a good accuracy on both ends thereof. In this state, the capsule is loaded between the connection ports 13a and 13b of the body 1, the connection ports 13a, 13b and the holes 9a, 9b made on both ends of the capsule C are in communication with each other. Both ends of the capsule C are pressed by peripheral edges 21a, 21b of the connection ports 13a, 13b and intensely put into an intimate contact with the peripheral edges 21a and 21b.

In the state described above, when air is inhaled from the inhaling the port 16, the suction valve 17 disposed to the second air passageway 15 is opened by the suction force and air is introduced from the hole 9b of the capsule 9 to the inside of the capsule C. The same time, the peroral powder P in the capsule C is sucked out from the hole 9a of the capsule C through the first air passageway 14 to the inhaling port 16, and dosed through the oral cavity put at the inhaling port 16 into a user's body.

In this case, since the holes 9a, 9b of the capsule C in communication with the suction ports 13a, 13b have a size substantially identical with or larger than the opening diameter of the connection ports 13a, 13b, the air introduced from the second air passageway 15 smoothly passes through the inside of the capsule C and flows to the first air passageway 14, so that the peroral powder P in the capsule C can be carried by the air stream with no residues to the inhaling port 16. In addition, when the suction valve 17 that introduces air from the second air passageway 15 into the capsule C is opened, since the disk-like poppet 19 advances from the hole 9b of the capsule C to the inside of the capsule C, and the poppet 19 causes the air introduced from the second air passageway 15 into the capsule C to flow inward at a high flow speed uniformly along the periphery of the hole 9b of the capsule C, the peroral powder P in the capsule C can be sucked out thoroughly.

Further, since both ends of the capsule C loaded between the connection ports 13a, 13b are pressed by the peripheral edges 21a, 21b of both of the connection ports 13a, 13b and intensely put into an intimate contact to the peripheral edges 21a, 21b, the peroral powder P in the capsule C can be prevented from leaking through the holes 9a, 9b made on both ends of the capsule C and scattering into the body 1. Further, when breath is erroneously blown inward from the inhaling port 16, since the suction valve 17 formed in the second air passageway 15 does not open, there is no possibility that the peroral powder P in the capsule C flows to the outside through the second air passageway 15. In addition, when the breath is blown from the inhaling port 16, since the inner pressure of the capsule C increases to exert a force of urging both ends of the capsule C from the inside to the peripheral edges 21a, 21b of the connection port 13a, 13b, the intimate contact between the both ends of the capsule C and the peripheral edges 21a, 21b is further increased to keep air tightness therebetween, scattering of the peroral powder P in the capsule C into the body 1 can also be prevented reliably, Accordingly, in a case where the peroral powder P is a powdery medicine to be dosed into the lungs of a patient suffering from asthma, etc., a predetermined amount of the powdery medicine necessary for the therapy can be dosed reliably. Further, the capsule C emptied after sucking out the peroral powder P can be ejected easily by merely retracting the capsule holder 2 for holding capsule C from the inside of the body as shown in FIG. 1 to FIG. 3.

Example 2

Figure 7:
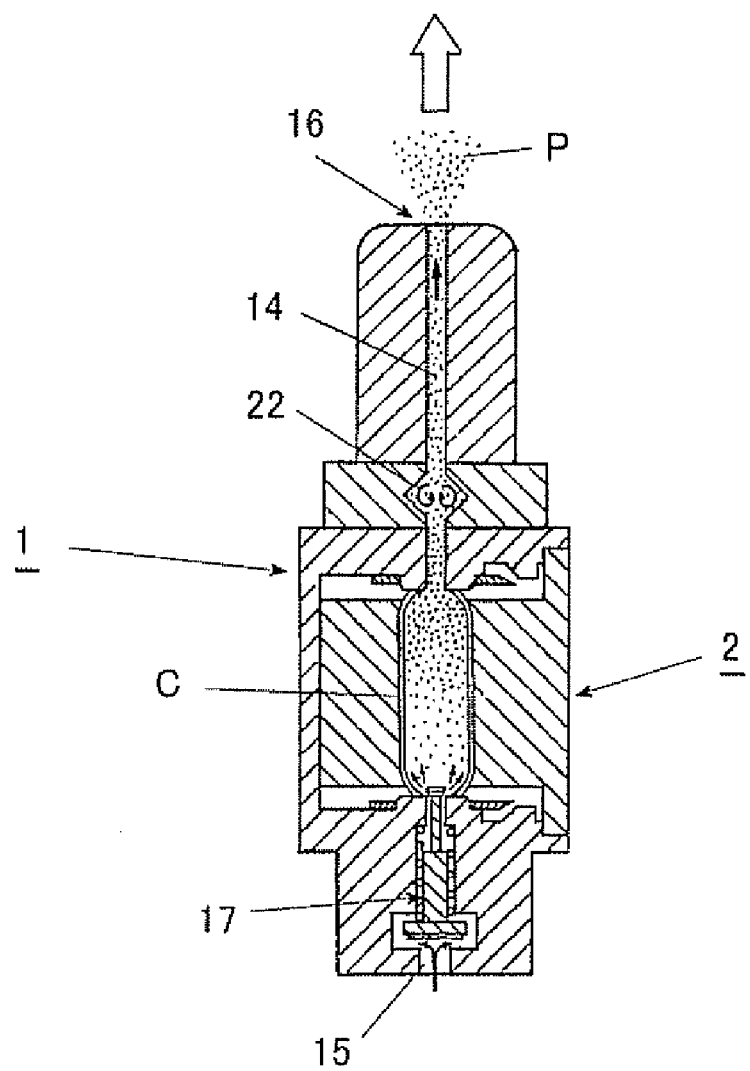
FIG. 7 is a cross sectional view showing another example of a peroral powder delivery device according to the invention.
Figure 8:
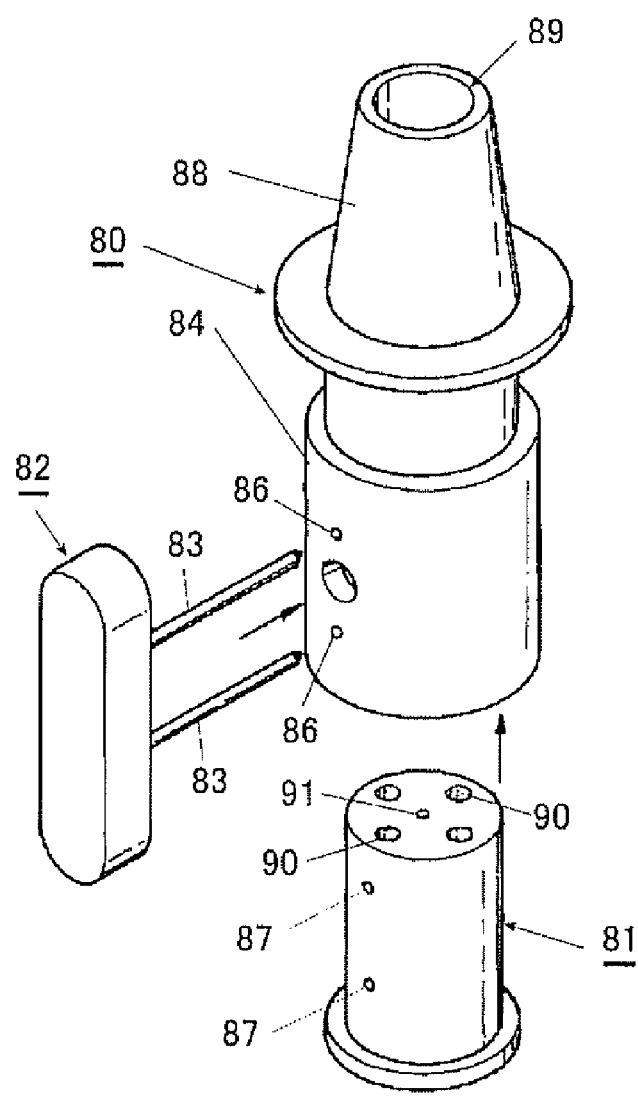
FIG. 8 is an external view of an existent example.
Figure 9:
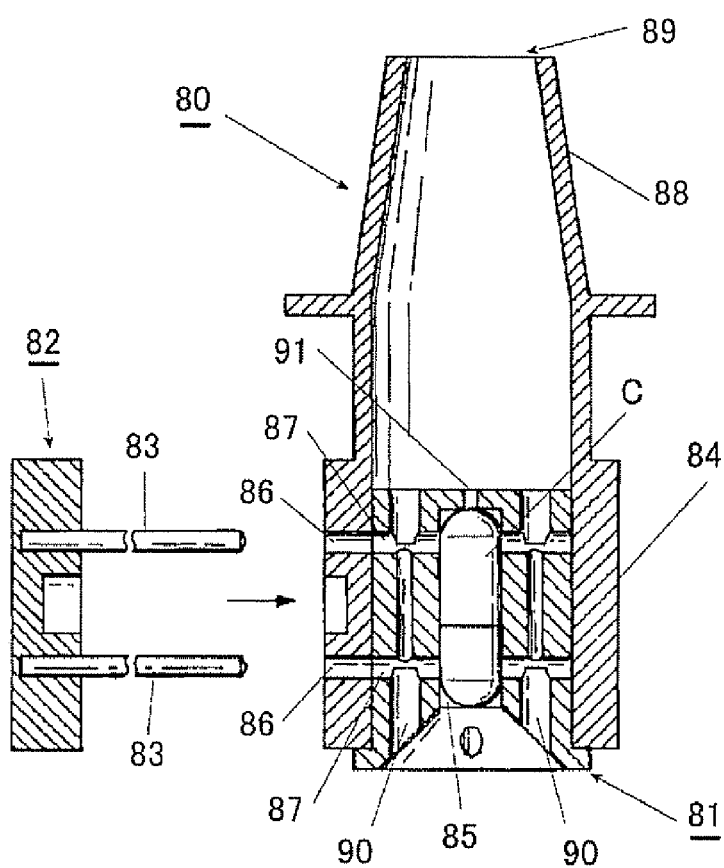
FIG. 9 is a cross sectional view of the existent example.

FIG. 7 is a cross sectional view showing another example of a peroral powder delivery device according to the invention. In the delivery device of this example, a mixer chamber 22 is formed in the first air passageway 14 for generating a turbulent flow to the air inhaled from the inhaling port 16, thereby separating and dispersing the particle of the peroral powder P inhaled from the inside of the capsule C together with the air. Since other constitutions are in common with those for the delivery device shown in FIG. 1 to FIG. 6, common portions carry identical reference numerals, for which detailed descriptions are to be omitted.

While a powdery medicine to be dosed into lungs through an oral cavity are in the form of a fine powder such as to be carried together with breath through a trachea to lungs, in a case where the separatability and the dispersibility of the particle are poor, the amount carried by the breath to the lungs is decreased to result in a disadvantage that the powdery medicine of a necessary amount can not be dosed. Then, in the peroral powder delivery device in FIG. 7, the mixer chamber 22 for separating and dispersing the grains of the peroral powder P inhaled from the inside of the capsule C is disposed in the first air passageway 14, so that the powdery medicine to be dosed into the lungs can be carried reliably by the breath into the lungs. The peroral powder delivery device of FIG. 7 is not restricted to the use for the powdery medicine but can also be used for application of dosing powdery food such as powder supplement and powdery drink through the oral cavity.

What is claimed is:

1. A peroral powder delivery device to deliver a unit dose of a peroral powder through an oral cavity in which
    a capsule holder for holding a capsule that contains a peroral powder and loading the capsule, the capsule holder is attached into a body so as to be capable of advancing into and retracting from the inside of the body in a direction perpendicular to the longitudinal direction of the capsule held by the capsule holder,
    the body has a cutter blade for cutting both ends of the capsule when it advances into the body while being held by the capsule holder and making holes on both ends of the capsule, and a first air passageway having a connection port in communication with a hole made on one end of the capsule when the capsule is loaded in the body and a second air passageway having a connection port in communication with a hole made on the other side of the capsule,
    the first air passageway has an inhaling port for inhaling the peroral powder in the capsule,
    the second airpassageway has a suction valve which opens by the suction force or inhalation force from the inhaling port to introduce air into the capsule, and
    the suction valve has a disciform poppet that protrudes from the connection port of the second air passageway and advances from the hole of the capsule in communication with the connection port to the inside of the capsule when the valve is opened,
    wherein the distance between the connection port of the first air passageway and the connection port of the second air passageway is set shorter than the length of the capsule after the both ends have been cut by the cutter blade,
    such that both ends of the capsule loaded therebetween are urged by peripheral edges of both of the connection ports.

2. A peroral powder delivery device according to claim 1, wherein
    the capsule is held in a recessed groove formed on the capsule holder, as being slidable in the longitudinal direction of the capsule, and a positioning guide is disposed for sliding the capsule that advances into the body being held by the capsule holder in the longitudinal direction and for guiding both ends of the capsule to be cut by the cutter blade such that both ends of the capsule situate at predetermined positions.

3. A peroral powder delivery device according claim 2, wherein the diameter of the holes made to both ends of the capsule by the cutter blade is set to a size substantially identical with or larger than the opening diameter for each of the connection ports in communication with the hole.

4. A peroral powder delivery device according to claim 2, wherein the cutter blade comprises a pair of blades secured in parallel with each other with the blade tips being directed in the direction opposing to the advancing direction of the capsule that advances into the body being held by the capsule holder, the positioning guide comprises a pair of protrusions, and a pocket is formed between the cutter blade and the protrusion as the positioning guide for discharging cut ends of the capsule cut by the blade.

5. A peroral powder delivery device according to claim 1, wherein a mixer chamber is formed in the first air passageway for generating a turbulent flow to the air inhaled from the inhaling port thereby finely separating and dispersing grains of the peroral powder inhaled together with air from the inside of the capsule.

\* \* \* \* \*